United States Patent [19]
Mitta et al.

[11] Patent Number: 5,908,772
[45] Date of Patent: Jun. 1, 1999

[54] GENE ENCODING LACTO-N-BIOSIDASE

[75] Inventors: Masanori Mitta, Tsuzuki-gun; Mutsumi Sano, Otsu; Ikunoshin Kato, Uji, all of Japan

[73] Assignee: Takara Shuzo Co., Ltd., Kyoto-fu, Japan

[21] Appl. No.: 08/637,899

[22] Filed: Apr. 26, 1996

[30] Foreign Application Priority Data

Apr. 27, 1995 [JP] Japan .................................. 7-129731

[51] Int. Cl.⁶ ............................. C12N 15/56; C12N 9/24; C12N 15/63; C12N 1/21
[52] U.S. Cl. ........................ 435/200; 435/71.1; 435/71.2; 435/172.3; 435/252.3; 435/320.1; 435/325; 435/419; 536/23.2; 536/23.7; 536/23.1
[58] Field of Search ................... 536/23.2, 23.7, 536/23.1; 435/71.1, 71.2, 200, 172.3, 252.3, 240.2, 320.1, 325, 419

[56] References Cited

U.S. PATENT DOCUMENTS 5,395,757  3/1995  Hayakawa et al. ........................ 435/84

FOREIGN PATENT DOCUMENTS 5-252946  10/1993  Japan .
6-153944   6/1994  Japan .
8-53487    2/1996  Japan .

OTHER PUBLICATIONS

Lemp et al., J. of Biological Chemistry, 265: 15606–15610 (1990).

Proc. Natl. Acad. Sci. USA, Mutsumi Sano et al., An enzyme releasing lacto–N–biose . . . , vol. 89, pp. 8512–8516 (1992).

The Journal of Biological Chemistry, Mutsumi Sano et al., Purification and Characterization . . . , vol. 268, pp. 18560–18566 (1993).

*Primary Examiner*—Rebecca E. Prouty
*Attorney, Agent, or Firm*—Birch, Stewart, Kolasch & Birch, LLP

[57] ABSTRACT

An isolated DNA having a sequence encoding a polypeptide possessing lacto-N-biosidase activity or functionally equivalent variants thereof; and a method for producing a polypeptide possessing lacto-N-biosidase activity or functionally equivalent variants thereof using the isolated DNA by recombinant DNA technology.

15 Claims, 1 Drawing Sheet

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 639 amino acids
      (B) TYPE: amino acid
      (C) STRANDEDNESS: single
      (D) TOPOLOGY: linear    (ii) MOLECULE TYPE: peptide    (xi) SEQUENCE DESCRIPTION: SEQ ID NO:1:

```
Met Asp Met Arg Met Ala Arg Arg Arg Thr Ile Gly Ala Val Val
 1               5                  10                  15

Thr Ala Leu Ala Ala Ala Leu Leu Pro Trp Gln Ser Ala Thr Ala
                20                  25                  30

Glu Gly Gly Ser Ala Ala Ala Pro Pro Glu Val Leu Pro Thr
                35                  40                  45

Leu Arg Glu Trp Gln Gly Gly Gln Gly Glu Phe Thr Leu Thr Asp
                50                  55                  60
```

-continued

```
Arg Ala Gly Ile Val Leu Asp Gly Val Arg Asp Ser Arg Thr Ala
             65                  70                  75
Ala Asp Ala Arg Arg Phe Ala Gly Glu Leu Asn Gly Lys Ala Ser
             80                  85                  90
Val Ser Gln Gly Arg Ala Ala Arg Pro Gly Asp Ile Val Leu Arg
             95                 100                 105
Gln Asp Pro Ala Gln Lys Gly Leu Leu Gly Ala Glu Gly Tyr Arg
            110                 115                 120
Leu Thr Val Gly Thr Arg Ile Thr Val Thr Ala Ala Thr Ser Thr
            125                 130                 135
Gly Val Phe Tyr Gly Thr Arg Thr Val Leu Gln Leu Leu Asn Asp
            140                 145                 150
Asp Gly Arg Ala Ala Arg Gly Ser Ala Thr Asp Val Pro Ala Tyr
            155                 160                 165
Arg Glu Arg Gly Val Gly Val Cys Ala Cys Tyr Ile Asn Ile Ser
            170                 175                 180
Thr Gln Trp Phe Glu Arg Leu Met Lys Asp Met Ala Ser Gln Lys
            185                 190                 195
Leu Asn Gln Leu Trp Ile Glu Ala Lys Val Lys Ser Asp Thr Asp
            200                 205                 210
Pro Ala Ser Ala Phe Trp Gly Tyr Tyr Thr Lys Pro Gln Val Arg
            215                 220                 225
Thr Leu Val Ala Met Ala Arg Lys Tyr His Ile Glu Leu Val Pro
            230                 235                 240
Glu Ile Asn Ser Pro Gly His Met Asp Thr Tyr Leu Glu Asn His
            245                 250                 255
Pro Glu Leu Gln Leu Lys Asp Arg Asp Gly Val Ala Ser Pro Pro
            260                 265                 270
Arg Leu Asp Ile Ser Arg Pro Glu Ala Leu Ala Tyr Tyr Thr Ser
            275                 280                 285
Met Val Asp Glu Ala Leu Lys Val Trp Asp Ser Arg Tyr Trp His
            290                 295                 300
Met Gly Ala Asp Glu Tyr Met Ile Gly Ser Ser Tyr Pro Asp Tyr
            305                 310                 315
Pro Gln Leu Gln Ala Ala Ala Arg Ala Lys Phe Gly Ala Ser Ala
            320                 325                 330
Thr Pro Asp Asp Leu Phe Thr Asp Phe Ile Asn Gln Val Asn Ala
            335                 340                 345
His Val Lys Ala Asp Gly Arg Ser Leu Arg Ile Trp Asn Asp Gly
            350                 355                 360
Leu Ala Gly Lys Asn Ala Val Val Pro Leu Asp Arg Asp Ile Thr
            365                 370                 375
Val Glu His Trp Leu Ser Gly Gly Ser Ile Gln Gln Pro Ser Ser
            380                 385                 390
Leu Leu Ala Glu Gly Arg Pro Val Met Asn Ser Ala Tyr Ser Leu
            395                 400                 405
Tyr Leu Val Arg Gly Gly Phe Thr Met Gln Thr Gln Lys Leu Tyr
            410                 415                 420
Glu Ser Asp Trp Thr Pro Leu Arg Phe Glu Gly Gln Thr Leu Thr
            425                 430                 435
Gln Gly Ala Ala Asn Leu Thr Gly Ala Lys Ile Ser Leu Trp Pro
            440                 445                 450
Asp Ser Ala Ala Ala Glu Thr Glu Asn Glu Val Glu Thr Lys Val
            455                 460                 465
```

```
Phe Met Pro Leu Arg Phe Val Ala Gln Ala Thr Trp Gly Gly Pro
            470                 475                 480

Lys Pro Ser Pro Thr Tyr Ala Gly Phe Glu Ala Leu Ala Arg Lys
            485                 490                 495

Ile Gly His Ala Pro Gly Trp Glu Asn Thr Asp Arg Thr Pro Leu
            500                 505                 510

Ala Asp Gly Thr Tyr Arg Leu Thr Thr Gly Ala Lys Ala Leu Ala
            515                 520                 525

Pro Thr Ala Asp Ala Gly Val Ser Leu Val Lys Asn Ser Ala Ala
            530                 535                 540

Ser Trp Ala Leu Thr Ala Thr Ala Asp Gly Tyr Tyr Thr Val Arg
            545                 550                 555

Ser Thr Glu Ser Gly Gln Cys Leu Asp Ala Val Arg Gly Lys Lys
            560                 565                 570

Tyr Leu Gly Ala Pro Leu Glu Val Gly Ala Glu Leu Ser Leu Ala
            575                 580                 585

Asn Cys Ser Thr Thr Ala Arg Thr Gln Arg Trp Gln Leu Asp Thr
            590                 595                 600

Gly Ala Gly Ala Leu Thr Leu Arg Asn Ala Ile Ser Gln Leu His
            605                 610                 615

Leu Thr Glu Arg Ala Ser Asp Gly Ala Ala Val Gln Thr Thr Gly
            620                 625                 630

Ala Thr Arg Leu Thr Ala Arg Ala Ala
            635
```

(2) INFORMATION FOR SEQ ID NO:2:

(i) SEQUENCE CHARACTERISTICS:
        (A) LENGTH: 1917 base pairs
        (B) TYPE: nucleic acid
        (C) STRANDEDNESS: double
        (D) TOPOLOGY: linear     (ii) MOLECULE TYPE: genomic DNA     (vi) ORIGINAL SOURCE:
        (A) ORGANISM: Streptomyces sp.
        (B) STRAIN: 142

(ix) FEATURE:
        (A) NAME/KEY: CDS
        (B) LOCATION: 1..1917
        (C) IDENTIFICATION METHOD: E     (xi) SEQUENCE DESCRIPTION: SEQ ID NO:2:

```
ATGGACATGC GGATGGCAAG ACGAAGGACC ATCGGAGCCG TGGTGACGGC GCTCGCCGCC    60

GCGCTGCTGC CCTGGCAGAG CGCGACGGCC GAGGGCGGCT CGGCCGCCGC GGCCCCGCCC   120

GAGGTGCTGC CCACGCTCCG CGAATGGCAA GGCGGTCAGG GCGAGTTCAC GCTCACCGAT   180

CGGGCCGGAA TCGTGCTGGA CGGGGTGCGG GACAGTCGTA CGGCCGCCGA CGCACGCCGA   240

TTCGCCGGCG AACTGAACGG CAAGGCGTCG GTGTCACAGG GCCGCGCGGC CCGTCCCGGG   300

GACATCGTGC TGCGCCAGGA CCCGGCCCAG AAGGGTCTGT TGGGCGCGGA AGGCTACCGG   360

CTCACGGTCG GCACCCGTAT CACTGTCACC GCCGCGACCT CCACCGGCGT GTTCTACGGC   420

ACCCGGACCG TCCTCCAGCT GCTGAACGAC GACGGCCGCG CCGCGCGGGG TTCGGCGACC   480

GACGTACCCG CGTACCGCGA GCGCGGAGTC GGGGTCTGCG CCTGCTACAT CAACATATCG   540

ACACAGTGGT TCGAGCGGCT GATGAAGGAC ATGGCGTCGC AGAAGCTCAA CCAGCTGTGG   600

ATCGAGGCCA AGGTCAAGAG CGACACCGAC CCGGCTTCGG CGTTCTGGGG CTACTACACC   660
```

```
AAGCCGCAGG TCCGCACGCT GGTCGCGATG GCCCGGAAGT ACCACATCGA GCTCGTGCCG        720

GAGATCAACT CGCCCGGCCA CATGGACACC TACCTGGAGA ACCACCCGGA GCTCCAGCTC        780

AAGGACCGGG ACGGTGTCGC CTCCCCGCCC CGGCTCGACA TCTCCCGGCC CGAGGCGCTG        840

GCGTACTACA CCTCGATGGT CGACGAGGCG CTGAAGGTCT GGGACAGCCG GTACTGGCAC        900

ATGGGCGCCG ACGAGTACAT GATCGGCTCC TCCTACCCGG ACTACCCCCA GCTGCAGGCC        960

GCGGCACGCG CGAAGTTCGG TGCGTCGGCG ACCCCCGACG ATCTCTTCAC CGACTTCATC       1020

AACCAGGTCA ACGCGCATGT GAAGGCGGAC GGCAGGTCGC TGCGGATCTG GAACGACGGG       1080

CTCGCCGGCA AGAACGCCGT TGTCCCGCTG GACCGTGACA TCACCGTCGA GCACTGGCTG       1140

AGCGGCGGCT CCATCCAGCA GCCGTCCTCG CTGCTCGCCG AGGGGCGGCC GGTCATGAAC       1200

TCCGCCTACT CCCTCTACCT GGTGCGCGGC GGATTCACGA TGCAGACCCA GAAGCTGTAC       1260

GAGAGCGACT GGACGCCGTT GCGCTTCGAG GGGCAGACGC TGACCCAGGG GGCGGCGAAC       1320

CTCACCGGCG CGAAGATCAG CCTGTGGCCG GACAGTGCGG CGGCCGAGAC GGAGAACGAG       1380

GTCGAGACGA AGGTCTTCAT GCCGCTGCGT TTCGTGGCGC AGGCGACCTG GGGCGGCCCG       1440

AAGCCGAGCC CGACGTACGC CGGTTTCGAG GCGCTCGCCC GGAAGATCGG TCACGCGCCG       1500

GGCTGGGAGA ACACCGACCG CACGCCGCTC GCCGACGGTA CGTACCGGCT GACCACGGGC       1560

GCGAAGGCGC TGGCCCCCAC GGCGGACGCG GGCGTGTCCC TGGTCAAGAA CAGCGCGGCC       1620

TCCTGGGCGC TGACGGCGAC CGCCGACGGG TACTACACGG TGCGGTCCAC GGAGAGCGGT       1680

CAGTGCCTGG ACGCGGTGCG CGGCAAGAAG TACCTGGGCG CGCCGCTGGA GGTGGGGGCG       1740

GAGCTGTCAC TCGCGAACTG CTCGACGACG GCACGTACCC AGCGCTGGCA GCTGGACACC       1800

GGGGCGGGTG CGCTGACGCT GCGCAACGCG ATCTCGCAGC TGCATCTGAC GGAGCGGGCG       1860

TCGGACGGCG CCGCGGTGCA GACGACGGGA GCGACCCGGC TGACGGCGCG CGCCGCC         1917

(2) INFORMATION FOR SEQ ID NO:3:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (v) FRAGMENT TYPE: N-terminal fragment (xi) SEQUENCE DESCRIPTION: SEQ ID NO:3:

Ala Ala Arg Pro His Glu Val Leu Pro Thr Leu Arg Glu Trp Gln
1               5                   10                  15
Gly Gly Thr (2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:4:

GCSMGSCCSC AYGARGT                                                       17

(2) INFORMATION FOR SEQ ID NO:5:
```

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: other nucleic acid (synthetic DNA)

(xi) SEQUENCE DESCRIPTION: SEQ ID NO:5:

CCSCAYGARG TSCWNCC                                                    17

(2) INFORMATION FOR SEQ ID NO:6:

(i) SEQUENCE CHARACTERISTICS:
         (A) LENGTH: 44 base pairs
         (B) TYPE: nucleic acid
         (C) STRANDEDNESS: single
         (D) TOPOLOGY: linear (ii) MOLECULE TYPE: other nucleic acid (synthetic DNA)

(xi) SEQUENCE DESCRIPTION: SEQ ID NO:6:

GCCGCCCGCC CSCACGARGT CCTSCCSACC CTSGACGAGG CCCA                       44

(2) INFORMATION FOR SEQ ID NO:7:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (v) FRAGMENT TYPE: intermediary fragment (xi) SEQUENCE DESCRIPTION: SEQ ID NO:7:

Ala Ala Arg Pro Gly Asp Ile Val Leu Arg
 1               5                   10

(2) INFORMATION FOR SEQ ID NO:8:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (v) FRAGMENT TYPE: intermediary fragment (xi) SEQUENCE DESCRIPTION: SEQ ID NO:8:

Gln Trp Asn Asp Gly Leu Ala Gly Lys
 1               5

(2) INFORMATION FOR SEQ ID NO:9:

(i) SEQUENCE CHARACTERISTICS:
         (A) LENGTH: 12 amino acids
         (B) TYPE: amino acid
         (C) STRANDEDNESS: single
         (D) TOPOLOGY: linear (ii) MOLECULE TYPE: peptide (v) FRAGMENT TYPE: intermediary fragment (xi) SEQUENCE DESCRIPTION: SEQ ID NO:9:

Ser Gln Leu Asp Thr Gly Ala Gly Ala Leu Thr Leu (2) INFORMATION FOR SEQ ID NO:10:

(i) SEQUENCE CHARACTERISTICS:
        (A) LENGTH: 24 amino acids
        (B) TYPE: amino acid
        (C) STRANDEDNESS: single
        (D) TOPOLOGY: linear     (ii) MOLECULE TYPE: peptide     (v) FRAGMENT TYPE: intermediary fragment     (xi) SEQUENCE DESCRIPTION: SEQ ID NO:10:

```
Asp Ile Thr Val Glu His Ala Leu Ser Gly Gly Ser Ile Gln Gln
  1               5                  10                  15
Pro Ser Ser Leu Leu Ala Glu Gly Pro
                20
```

(2) INFORMATION FOR SEQ ID NO:11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear     (ii) MOLECULE TYPE: other nucleic acid (synthetic DNA)

(xi) SEQUENCE DESCRIPTION: SEQ ID NO:11:

```
CARTGGAAYG AYGGNYTNGC NGGNAAR                                27
```

(2) INFORMATION FOR SEQ ID NO:12:

(i) SEQUENCE CHARACTERISTICS:
        (A) LENGTH: 72 base pairs
        (B) TYPE: nucleic acid
        (C) STRANDEDNESS: single
        (D) TOPOLOGY: linear     (ii) MOLECULE TYPE: other nucleic acid (synthetic DNA)

(xi) SEQUENCE DESCRIPTION: SEQ ID NO:12:

```
GAYATHACNG TNGARCAYGC NYTNWSNGGN GGNWSNATHC ARCARCCNWS NWSNYTNYTN   60
GCNGARGGNC CN                                                       72
```

(2) INFORMATION FOR SEQ ID NO:13:

(i) SEQUENCE CHARACTERISTICS:
        (A) LENGTH: 39 base pairs
        (B) TYPE: nucleic acid
        (C) STRANDEDNESS: single
        (D) TOPOLOGY: linear     (ii) MOLECULE TYPE: other nucleic acid (synthetic DNA)

(xi) SEQUENCE DESCRIPTION: SEQ ID NO:13:

```
AGAAGCTTGG CCATGGCCGC GGCCCCGCCC GAGGTGCTG                  39
```

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (ii) MOLECULE TYPE: other nucleic acid (synthetic DNA)

-continued (xi) SEQUENCE DESCRIPTION: SEQ ID NO:14:

GTCCTGGCGC AGCACGATGT C                                          21

GENE ENCODING LACTO-N-BIOSIDASE

BACKGROUND OF THE INVENTION

1. Field of the Invention

The present invention relates to a gene encoding a polypeptide possessing lacto-N-biosidase activity, and to a method for producing a polypeptide possessing lacto-N-biosidase activity by the use of the gene.

2. Discussion of the Related Art

Considerable attention has been given in recent years to various physiological functions of the sugar chains of so called complex carbohydrates, such as glycoproteins and glycolipids existing on the surface of animal cells. A glycosidase with high specificity has become a very useful tool in the research of structures and biological activities of the sugar chains. Two types of sugar chains, type 1 structure (Gal β1-3GlcNAc β1-) and type 2 structure (Gal β1-4GlcNAc β1-) are frequently found in N- and O-linked sugar chains of glycoproteins, or in sugar chains of glycolipids. In the structural analyses of these sugar chains, lacto-N-biosidase is used as a very useful reagent, because lacto-N-biosidase specifically acts on the type 1 structure and is capable of releasing lacto-N-biose (Gal β1-3GlcNAc) from the nonreducing terminus.

With respect to lacto-N-biosidase, those produced by Streptomyces strains are known [Proceedings of the National Academy of Sciences of the USA, 89, 8512–8516 (1992); Journal of Biological Chemistry, 268, 18560–18566 (1993)].

A method for producing lacto-N-biosidase by culturing such lacto-N-biosidase producing Streptomyces bacteria requires tedious and time-consuming purification procedures because the bacteria also produce other enzymes such as protease, β-N-acetylglucosaminidase and α-1,3/4-fucosidase. Also, in order to induce enzyme production, it is required to add L-fucose, swine gastric mucin, etc. Hence, there has been a need for a method producing lacto-N-biosidase at low cost and high purity.

A method for purification of lacto-N-biosidase from a culture of Streptomyces strains is known (Japanese Patent Laid-Open No. 6-153944). However, neither the amino acid sequence of lacto-N-biosidase nor the gene sequence encoding the enzyme has so far been elucidated, thereby impeding the production of lacto-N-biosidase by recombinant DNA technology.

SUMMARY OF THE INVENTION

An object of the present invention is to provide a gene encoding a polypeptide possessing lacto-N-biosidase activity.

Another object of the present invention is to provide an advantageous method for producing a polypeptide possessing lacto-N-biosidase activity on an industrial scale using the gene of the invention.

In general, genes of actinomycetes have high G+C contents, thereby making the isolation of a desired gene extremely difficult. This is reflected in the fact that the number of genes with established sequences in actinomycetes is markedly smaller than that in other microorganisms.

In order to elucidate the amino acid sequence of lacto-N-biosidase and the gene sequence encoding lacto-N-biosidase, the present inventors conducted intensive studies with a lacto-N-biosidase producing actinomycete strain (Streptomyces sp142) and have first succeeded in establishing the entire base sequence of the gene and the amino acid sequence of lacto-N-biosidase. The present inventors have also succeeded in developing an advantageous method for industrial scale production of lacto-N-biosidase using the gene of the invention. Based upon these facts, the present invention has been completed.

The gist of the present invention is concerned with:

(1) An isolated DNA having a sequence encoding a polypeptide possessing lacto-N-biosidase activity or functionally equivalent variants thereof;

(2) An isolated DNA capable of hybridizing to any one of isolated DNAs as defined in (1) above, wherein the isolated DNA encodes a polypeptide possessing lacto-N-biosidase activity or functionally equivalent variants thereof;

(3) A recombinant DNA which comprises a DNA sequence encoding a polypeptide possessing lacto-N-biosidase activity or functionally equivalent variants thereof;

(4) An expression vector which comprises a recombinant DNA comprising a DNA sequence encoding a polypeptide possessing lacto-N-biosidase activity or functionally equivalent variant, wherein the expression vector is capable of propagating in a procaryotic or eucaryotic cell;

(5) A cell of a procaryote or eucaryote transformed with an expression vector which comprises a DNA sequence encoding a polypeptide possessing lacto-N-biosidase activity or functionally equivalent variants thereof; and (6) A method for producing a polypeptide possessing lacto-N-biosidase activity or functionally equivalent variants thereof, comprising the steps of:

(a) culturing a transformant obtained by introducing an expression vector to a host cell, the expression vector containing a DNA sequence of any one of isolated DNAs as defined in (1) and (2) above; and (b) isolating the polypeptide possessing lacto-N-biosidase activity or functionally equivalent variants thereof from the culture obtained in Step (a).

The entire amino acid sequence of lacto-N-biosidase and the gene sequence encoding the enzyme have first been provided by the present invention, thereby enabling an advantageous, industrial-scale production of a polypeptide possessing lacto-N-biosidase activity using recombinant DNA technology.

BRIEF DESCRIPTION OF THE DRAWING

FIG. 1 shows restriction endonuclease maps of (A) PstI-KpnI region in insertion PstI fragment of pULNBP80; and (B) MluI-PstI region in insertion PstI fragment of pULNBP2-17, both (A) and (B) indicating the location of the lacto-N-biosidase gene in bold line.

DETAILED DESCRIPTION OF THE INVENTION

The term "lacto-N-biosidase" as used in the present specification refers to an enzyme that is capable of specifically acting on a sugar chain having a structure represented by Gal β1-3GlcNAc β1-R (R is a sugar residue), and specifically catalyzing the hydrolysis of lacto-N-bioside bond only. The term "possessing lacto-N-biosidase activity" as used herein means that the activity of lacto-N-biosidase as determined by the method described in Proceedings of the National Academy of Sciences of the USA, 89, 8512–8516 (1992) is not less than $1 \times 10^{-7}$ units. The term "a polypeptide possessing lacto-N-biosidase activity" as used herein includes not only native lacto-N-biosidase but also its variations due to modification of amino acid sequence by, for example, deletion, substitution, insertion, or addition of amino acid(s), as long as they retain lacto-N-biosidase activity.

"Native lacto-N-biosidase" as used herein includes, but not limited to, those produced by Streptomyces strains. Also included are those derived from other microorganisms, such as bacteria, yeasts, fungi, Ascomycetes, and Basidiomycetes, and those derived from plants and animals.

The term "functionally equivalent variant" as used herein is defined as follows:

A naturally-occurring protein can undergo amino acid deletion, insertion, addition, substitution and other variations in its amino acid sequence due to modifications, etc. of the protein itself in vivo or during purification, as well as those due to polymorphism and variation of the gene encoding it. It is a well-known fact that there are some such polypeptides which are substantially equivalent to variation-free proteins in terms of physiological and biological activity. A polypeptide structurally different from the corresponding protein, but having no significant functional difference from the protein is referred to as a functionally equivalent variant.

The same applies to polypeptides prepared by artificially introducing such variations to the amino acid sequence of a protein. Although more diverse variants can be thus obtained, the resulting variants are construed as functionally equivalent variants, as long as their physiological activity is substantially equivalent to that of the original variation-free protein.

For example, the methionine residue at the N-terminus of a protein expressed in *Escherichia coli* is reportedly often removed by the action of methionine aminopeptidase, but some such expressed proteins have the methionine residue and others not. However, the presence or absence of the methionine residue does not affect protein activity in most cases. It is also known that a polypeptide resulting from replacement of a particular cysteine residue with serine in the amino acid sequence of human interleukin 2 (IL-2) retains IL-2 activity [Science, 224, 1431 (1984)].

In addition, in producing a protein by gene engineering, the desired protein is often expressed as a fused protein. For example, the N-terminal peptide chain derived from another protein is added to the N-terminus of the desired protein to enhance the expression of the desired protein, or purification of the desired protein is facilitated by adding an appropriate peptide chain to the N- or C-terminus of the desired protein, expressing the protein, and using a carrier showing affinity for the peptide chain added.

Also, with regards to the codon (triplet base combination) determining a particular amino acid on the gene, 1 to 6 kinds are known to exist for each amino acid. Therefore, there can be a large number of genes encoding an amino acid sequence, though depending on the amino acid sequence. In nature, the gene is not stable, commonly undergoing nucleic acid variation. A variation on the gene may not affect the amino acid sequence to be encoded (silent variation); in this case, it can be said that a different gene encoding the same amino acid sequence has been produced. The possibility is therefore unnegligible that even when a gene encoding a particular amino acid sequence is isolated, a variety of genes encoding the same amino acid sequence are produced with generation of the organism containing it.

Moreover, it is not difficult to artificially produce a variety of genes encoding the same amino acid sequence by means of various gene engineering techniques.

For example, when the codon used on the natural gene encoding the desired protein is low in availability in the host used to produce the protein by gene engineering, the amount of protein expressed is sometimes insufficient. In this case, expression of the desired protein is enhanced by artificially converting the codon into another one of high availability in the host without changing the amino acid sequence encoded. It is of course possible to artificially produce a variety of genes encoding a particular amino acid sequence. Such artificially produced different polynucleotides are therefore included in the scope of the present invention, as long as an amino acid sequence disclosed herein is encoded.

Additionally, a polypeptide resulting from at least one change, such as deletion, addition, insertion or substitution, of one or more amino acid residues in the amino acid sequence of the desired protein commonly possesses an activity functionally equivalent to that of the desired protein; genes encoding such polypeptides are also included in the scope of the present invention, whether isolated from natural sources or produced artificially.

In general, functionally equivalent variants are often homologous to each other in terms of genes encoding them. Genes capable of hybridizing to a gene for the present invention, and encoding a polypeptide possessing lacto-N-biosidase activity, are therefore also included in the scope of the present invention.

The present invention is hereinafter described in detail with reference to lacto-N-biosidase derived from Streptomyces sp142.

The strain Streptomyces sp142 has been deposited under accession number FERM BP-4569 at the National Institute of Bioscience and Human-Technology, Agency of Industrial Science and Technology, Ministry of International Trade and Industry.

1) First, Streptomyces sp142 is cultured in accordance with the method described in the Proceedings of the National Academy of Sciences of the USA, 89, 8512–8516 (1992). Lacto-N-biosidase produced by the Streptomyces sp142 is then isolated and purified from the culture by, for example, the method described in the Journal of Biological Chemistry, 268, 18560–18566 (1993).

2) Second, information regarding a partial amino acid sequence of the purified lacto-N-biosidase is obtained. The partial amino acid sequence is determined over the region of 10 to 20 residues in the N-terminal amino acid sequence of lacto-N-biosidase by directly subjecting the purified lacto-N-biosidase to amino acid sequencing (Protein Sequencer 476A, produced by Applied Biosystems) based on Edman degradation by a conventional method. Alternatively, it is effective to conduct amino acid sequencing for a purified peptide fragment obtained by subjecting the purified lacto-N-biosidase to limited hydrolysis by the action of a protein hydrolase with high specificity, such as Achromobacter protease I or N-tosyl-L-phenylalanylchloromethylketone (TPCK)-trypsin, and separating and purifying the resulting peptide fragment by reversed-phase HPLC.

3) On the basis of the thus-obtained partial amino acid sequence information, the lacto-N-biosidase gene is cloned. For this purpose, a commonly used PCR or hybridization method is used.

a) On the basis of the partial amino acid sequence information, synthetic oligonucleotides are designed for use as Southern hybridization probes.

b) Separately, the genomic DNA of Streptomyces sp142 is completely digested with the appropriate restriction enzymes and subjected to agarose gel electrophoresis, and the resulting fragments are blotted onto a nylon membrane by a conventional method.

c) Hybridization of the separated DNA fragments with the synthetic oligonucleotides designed on the basis of the partial amino acid sequence information is conducted under commonly used conditions. For example, the nylon membrane is blocked in a prehybridization solution containing salmon sperm DNA, and each $^{32}$P-labeled synthetic oligonucleotide is added, followed by overnight incubation. After the nylon membrane is washed, an autoradiogram is taken to detect a DNA fragment that hybridizes to the synthetic oligonucleotide probe. The DNA fragment corresponding to the band detected is extracted and purified from the gel.

d) The thus-obtained DNA fragment, which hybridizes to the synthetic oligonucleotide probe, is inserted to a plasmid vector by a commonly used method. Useful plasmid vectors include, but are not limited to, pUC18, pUC19, pUC119 and pTV118N.

e) The recombinant plasmid is then introduced to a host to transform the host. When the host is *Escherichia coli*, it may be of a wild strain or a variant strain, as long as it is capable of transformation. This plasmid introduction can be achieved by a commonly used method, such as the method described at page 250 of the Molecular Cloning, A Laboratory Manual (T. Maniatis et al., Cold Spring Harbor Laboratory Press, 1982).

f) Next, a transformant harboring the desired DNA fragment is selected.

For this purpose, the characteristics of the plasmid vector are utilized. In the case of pUC19, for instance, colonies having a foreign gene introduced thereto are selected by selecting ampicillin-resistant colonies on an ampicillin-containing plate, or selecting ampicillin-resistant white colonies on a plate containing ampicillin, 5-bromo-4-chloro-3-indolyl-β-D-galactoside (X-Gal) and isopropyl-β-D-thiogalactopyranoside (IPTG).

g) The colony having a vector containing the desired DNA fragment is then selected out of the above population. This selection is achieved by using colony hybridization or plaque hybridization, chosen appropriately according to vector types. PCR methods are also applicable.

h) Once the vector containing the desired DNA fragment is selected, the base sequence of the desired DNA fragment inserted in this vector is determined by an ordinary method, such as the dideoxy chain terminator method [Proceedings of the National Academy of Sciences of the USA, 74, 5463 (1977)]. The thus-determined base sequence is compared with the N-terminal sequence, partial amino acid sequence, molecular weight, etc. of lacto-N-biosidase, to determine whether the base sequence represents the entire or partial portion of the desired lacto-N-biosidase gene. From the thus-obtained DNA fragment containing the lacto-N-biosidase gene, the structure of the lacto-N-biosidase gene and the entire amino acid sequence of lacto-N-biosidase are determined.

i) When the vector containing the desired DNA fragment does not contain the full-length lacto-N-biosidase gene, the desired full-length lacto-N-biosidase gene can be obtained by digesting the genomic DNA of Streptomyces sp142 with other restriction enzymes, obtaining the lacking portion from the digests by hybridization, etc. using a part of the DNA fragment obtained above as a probe, as described above, then joining the lacking portion.

In an attempt to clone the lacto-N-biosidase gene derived from Streptomyces sp142, the following various methods were conducted, but all failed to clone the desired gene.

1) PCR Method Using Cassette DNA

This method represents an approach to amplifying the desired DNA fragment in which a PCR reaction is carried out using a synthetic oligonucleotide primer designed on the basis of partial amino acid sequence information by a conventional method and another synthetic oligonucleotide primer (cassette primer) complementary to synthetic DNA having a known sequence (cassette DNA), in the presence of a template prepared by digesting the genomic DNA (extracted from Streptomyces sp142 by a conventional method) with appropriate restriction enzymes, then joining the cassette DNA.

The cassette DNA or cassette primer may be a product of Takara Shuzo Co., Ltd. The cassette DNA contains sequences corresponding to two kinds of cassette primers. It is known that the desired DNA fragment can be efficiently amplified by conducting a first PCR reaction using the primer distant from the restriction enzyme site, and conducting a second PCR reaction using the primer near the restriction enzyme site with a portion of the first PCR reaction mixture as a template. The present inventors attempted to obtain the gene of the present invention by this method. First, synthetic oligonucleotide primers LN-PN2-1 (SEQ ID NO:4) and LN-PN2-2 (SEQ ID NO:5) were synthesized on the bases of the N-terminus sequence LN-N2 (SEQ ID NO:3). The genomic DNA extracted from Streptomyces sp142 by a conventional method was digested with restriction enzymes Sau3AI, BmaHI, PstI and SalI, followed by ligation of the respective cassette DNA (produced by Takara Shuzo). Using these ligation products as templates, PCR reactions were carried out with a combination of LN-PN2-1 and the C1 primer (produced by Takara Shuzo). The PCR was conducted in accordance with the method described in "PCR Technology", ed. Erlich, HA, Stockton Press, 1989, using, for example, the Gene Amp Reagent Kit produced by Perkin-Elmer-Cetus Instruments. A thermal cycle of 94° C.×30 seconds, 55° C.×2 minutes and 72° C.×2 minutes was repeated in 30 cycles. Using a portion of this reaction mixture, additional PCR reaction was carried out with a combination of LN-PN2-2 and the C2 primer (produced by Takara Shuzo) under the same conditions as those described above. The reaction mixture was analyzed by agarose gel electrophoresis, and the base sequence of the amplified DNA fragment was determined using a commonly used method, but no sequences possibly representing the desired gene were detected, except the sequences of the synthetic DNAS.

2) Approach by PCR Method (2'-deoxy-7-deazaguanosine triphosphate (dc$^7$GTP)) Using Cassette DNA Using the same templates as those used in 1) above, a PCR reaction was carried out with a combination of LN-PN2-1 and the C1 primer (produced by Takara Shuzo). The PCR was conducted using the Gene Amp Reagent Kit and a mixture of dATP, dCTP, dTTP, dGTP and dc$^7$GTP in place of a mixture of dNTP, by repeating a thermal cycle of 94° C.×30 seconds, 55° C.×2 minutes and 72° C.×3 minutes in 25 cycles. Using a portion of this reaction mixture as a template, PCR reaction was carried out in the same cycles with a combination of LN-PN2-2 and the C2 primer (produced by Takara Shuzo) under the same thermal conditions as those described above, except that an ordinary dNTP mixture was used as a substrate. The reaction mixture was analyzed by agarose gel electrophoresis, and the base sequence of the amplified DNA fragment was determined using a commonly used method, but no sequences possibly representing the desired gene were detected except the sequences of the synthetic DNAs.

3) Synthetic DNA Hybridization Method

It is also a common practice to detect the desired DNA by designing a synthetic oligonucleotide on the basis of amino acid sequence information by a conventional method, and conducting hybridization. The present inventors attempted to detect the gene of the present invention by this method. As probes for Southern hybridization, synthetic oligonucleotides LN-PN2-2 (SEQ ID NO:5) and LN-PN2-3 (SEQ ID NO:6), both synthesized on the basis of the N-terminal sequence LN-N2 (SEQ ID NO:3), were used. The genomic DNA of Streptomyces sp142 was completely digested with restriction enzymes BmaHI, PstI, SacI and SalI and subjected to agarose gel electrophoresis to separate them, and the resulting fragments were blotted onto a nylon membrane by a conventional method. Hybridization was conducted under commonly used conditions. Specifically, the nylon membrane was blocked at 60° C. in a prehybridization solution containing 6× SSC, 0.5% SDS, 5× Denhardt's solution and 100 µg/ml salmon sperm DNA, and each $^{32}$P-labeled synthetic oligonucleotide was added, followed by overnight incubation at 40° C. for LN-PN2-2 or at 50° C. for LN-PN2-3. After the nylon membrane was twice washed with 2× SSC containing 0.1% SDS at room temperature for 30 minutes, an autoradiogram was taken to detect DNA fragments that hybridized to the respective synthetic oligonucleotide probes. When any of the two probes was used, a number of bands appeared on the lane for each restriction enzyme digest. The DNA fragments that hybridized to these probes were extracted from the gel by a commonly used method and were each inserted to a plasmid vector, followed by base sequencing by a commonly used method. Although some sequences homologous to the sequences of the synthetic DNAs were obtained, there was no amino acid sequence homology, nor was detected any sequence possibly representing the desired gene.

As stated above, it is quite difficult to clone the lacto-N-biosidase gene of the present invention from the genomic DNA of Streptomyces sp142. Because the genomic gene of Streptomyces sp142 has a high G+C content, it is likely to have a secondary structure, which can interfere with the progress of polymerase reaction and cause nonspecific annealing, resulting in the possibility of amplification of nonspecific DNA fragments in the PCR method or generation of nonspecific hybrids in the hybridization method. In consideration of these facts, the present inventors made extensive investigation, and first found that a portion of the desired lacto-N-biosidase gene can be hybridized by using particular synthetic oligonucleotides designed and synthesized on the basis of an internal partial amino acid sequence of lacto-N-biosidase as a probe for the hybridization method.

More specifically, synthetic oligonucleotides LN-P7 (SEQ ID NO:11) and LN-PN46-2 (SEQ ID NO:12) are synthesized on the basis of the partial amino acid sequences LN-7 (SEQ ID NO:8) and LN-46 (SEQ ID NO:10), respectively, and hybridization is conducted using these synthetic oligonucleotides as probes.

The genomic DNA of Streptomyces sp142 is completely digested with restriction enzymes BmaHI, PstI, SacI and SalI and subjected to agarose gel electrophoresis for separation, followed by blotting onto a nylon membrane by a conventional method. Hybridization can be conducted under commonly used conditions. For example, the nylon membrane is blocked at 65° C. in a prehybridization solution containing 6× SSC, 0.5% SDS, 5× Denhardt's solution and 100 µg/ml Pacific herring sperm DNA, and each $^{32}$P-labeled synthetic oligonucleotide is added, followed by overnight incubation at 65° C. After the nylon membrane is washed in 6× SSC at room temperature for 10 minutes, in 2× SSC containing 0.1% SDS at room temperature for 10 minutes, then in 0.2× SSC containing 0.1% SDS at 45° C. for 30 minutes, an autoradiogram is taken to detect DNA fragments that hybridize to the respective synthetic oligonucleotide probes. A number of bands that hybridized to the respective probes appeared at positions corresponding to about 8 kb for the BamHI digest, about 3 kb for the PstI digest, about 7.5 kb for the SacI digest, and about 1.8 kb for the SalI digest. These DNA sequences were extracted from the gel by a commonly used method, and inserted to a plasmid vector, followed by base sequencing by a commonly used method, e.g., the dideoxy chain terminator method. A sequence corresponding to a partial amino acid sequence of lacto-N-biosidase was detected, and a portion of the desired lacto-N-biosidase gene was successfully obtained. Of course, by conducting an additional procedure of the hybridization method using the thus-obtained gene fragment as a probe, the gene encoding the full-length of lacto-N-biosidase sequence can be cloned.

The thus-obtained entire base sequence of the gene for the lacto-N-biosidase produced by Streptomyces sp142 was determined to be as shown in SEQ ID NO:2, and the entire amino acid sequence deduced therefrom was determined to be as shown in SEQ ID NO:1. It should be noted that the numerous base sequences corresponding to SEQ ID NO:1, in addition to those corresponding to SEQ ID NO:2, are all included in the scope of the present invention. The genes of the present invention include the gene encoding a polypeptide possessing lacto-N-biosidase activity, and containing a portion of the amino acid sequence shown in SEQ ID NO:1, the gene encoding a polypeptide possessing lacto-N-biosidase activity, and containing a portion of the DNA sequence shown in SEQ ID NO:2, and the gene encoding a polypeptide possessing lacto-N-biosidase activity, and capable of hybridizing to these genes.

Using the entire lacto-N-biosidase gene whose entire base sequence has been determined as described above, or a portion thereof, as a probe for hybridization, DNA encoding a polypeptide possessing lacto-N-biosidase activity and high homology to the lacto-N-biosidase gene can be selected from a genomic DNA or cDNA library derived from an organism other than Streptomyces sp142. Hybridization can be conducted using commonly used conditions as described above, and genes showing different degrees of homology can be obtained by changing washing and other conditions.

To obtain the desired gene encoding a polypeptide possessing lacto-N-biosidase activity or functionally equivalent variant thereof by hybridization, the following method, for example, can be used.

First, chromosome DNA obtained from the desired gene source, or cDNA prepared from mRNA by means of reverse transcriptase, is joined to a plasmid or phage vector and introduced to a host to yield a library by a conventional method. The library is then cultured on a plate; the resulting colonies or plaques are each transferred onto a nitrocellulose or nylon membrane and subjected to denaturing treatment to immobilize the DNA to the membrane. This membrane is incubated in a solution containing a probe labeled with $^{32}$P or the like (the probe used may be any gene encoding the amino acid sequence shown in SEQ ID NO:1 or a portion thereof; for example, the gene shown in SEQ ID NO:2 or a portion thereof can be used), to form a hybrid between the DNA on the membrane and the probe. For example, the membrane with DNA immobilized thereon is subjected to hybridization with the probe in a solution containing 6× SSC, 1% sodium lauryl sulfate, 100 µg/ml salmon sperm DNA and 5× Denhardt's solution (containing bovine serum albumin, polyvinylpyrrolidone and Ficoll, each at 0.1%) at 65° C. for 20 hours. After hybridization, the nonspecifically adsorbed portion is washed down, followed by autoradiography, etc. to identify clones that formed a hybrid with the probe. This procedure is repeated until only a single clone has formed the hybrid. The clone thus obtained has a gene encoding the desired protein inserted therein.

The base sequence of the gene obtained is then determined by, for example, the following method, to confirm if the gene obtained is identical with the desired gene encoding a polypeptide possessing lacto-N-biosidase activity or functionally equivalent variant thereof.

When the recombinant is *Escherichia coli*, base sequencing for a clone obtained by hybridization can be achieved by culturing the *Escherichia coli* in a test tube, or the like, extracting the plasmid by a conventional method, digesting the extracted plasmid with restriction enzymes, separating the insert and subcloning it into M13 phage vector, or the like, and determining the base sequence by the dideoxy method. When the recombinant is a phage, basically the same procedure as that used above can be used to determine the base sequence. Basic experimental techniques for from cultivation to base sequencing are described in, for example, Molecular Cloning, A Laboratory Manual, T. Maniatis et al., Cold Spring Harbor Laboratory Press (1989).

To confirm the identity of the gene obtained as the desired gene encoding a polypeptide possessing lacto-N-biosidase activity or functionally equivalent variant thereof, the base sequence determined is compared with the base sequence of the lacto-N-biosidase gene of the present invention and the amino acid sequence shown in SEQ ID NO:1 in the sequence listing.

If the gene obtained does not contain the entire region encoding a polypeptide possessing lacto-N-biosidase activity or functionally equivalent variant thereof, the base sequence of the entire region encoding a polypeptide possessing lacto-N-biosidase activity or functionally equivalent variant thereof that hybridizes to the lacto-N-biosidase gene of the present invention can be determined by preparing a synthetic DNA primer from the gene obtained, and amplifying the lacking region by PCR or by screening the DNA library or cDNA library using the gene fragment obtained as a probe.

On the other hand, a primer for PCR reaction can be designed from the base sequence of the gene of the present invention. It is possible to detect a gene fragment highly homologous to the gene of the present invention or obtain the entire gene, by carrying out a PCR reaction using this primer.

For producing a polypeptide possessing lacto-N-biosidase activity using the lacto-N-biosidase gene of the present invention, the following method is advantageous.

First, a host is transformed with a vector containing the desired lacto-N-biosidase gene. This transformant is then cultured under commonly used conditions to produce a polypeptide possessing lacto-N-biosidase activity. As the case may be, the polypeptide is produced in the form of an inclusion body. Useful hosts include microorganisms, animal cells and plant cells.

It is advantageous to confirm expression by, for example, determining lacto-N-biosidase activity. Activity can be determined by the method described in the Proceedings of the National Academy of Sciences of the USA, 89, 8512–8516 (1992), using a recombinant *Escherichia coli* cell extract as an enzyme solution, as described above.

When the desired expression of lacto-N-biosidase is noted, lacto-N-biosidase can be efficiently produced by setting optimum conditions for lacto-N-biosidase expression as to medium composition, medium pH, culturing temperature, amount of inducer used, timing of induction, culturing time, etc., in cases where the transformant is *Escherichia coli*.

Lacto-N-biosidase can be purified from the transformant culture by an ordinary method. When the transformant, like *Escherichia coli*, intracellularly accumulates lacto-N-biosidase after cultivation, transformant cells are collected by centrifugation, disrupted by ultrasonication, or the like, and then subjected to centrifugation, etc. to yield a cell-free extract, which can be purified by common protein purification methods, such as salting-out and various chromatographies, including ion exchange, gel filtration, hydrophobic and affinity chromatographies. Depending on the host-vector system used, the expression product is extracellularly secreted by the transformant; in this case, the product can be purified from the culture supernatant in the same manner as that described above.

When lacto-N-biosidase is intracellularly produced by the transformant, various enzymes are also present in the cell, but purification of the lacto-N-biosidase is very easy, because such enzymes are present in trace amounts, relative to the amount of lacto-N-biosidase. When lacto-N-biosidase is extracellularly secreted, medium components, etc. are also present. However, these co-present substances normally contain almost no protein components that can interfere with lacto-N-biosidase purification; this is advantageous in that there is no need for the painstaking separating operation for purification of lacto-N-biosidase from the Streptomyces sp142 culture (containing $\alpha$-1,3/4-fucosidase, $\beta$-N-acetylglucosaminidase, etc., which are difficult to separate from lacto-N-biosidase) [Journal of Biological Chemistry, 257, 8205–8210 (1982)].

When the host is *Escherichia coli*, the expression product is sometimes formed as an insoluble inclusion body. In this case, cells are collected by centrifugation after cultivation, disrupted by ultrasonication, or the like, then subjected to centrifugation, etc. to separate the insoluble fraction containing the inclusion body. After being washed, the inclusion bodies are solubilized with a commonly used protein solubilizer, such as urea or guanidine hydrochloride, followed by purification by various chromatographies, such as ion exchange, gel filtration, hydrophobic and affinity chromatographies, as necessary, after which a refolding treatment by dialysis or dilution is conducted to yield the desired polypeptide retaining lacto-N-biosidase activity. This standard preparation may be purified by various chromatographies to yield a highly pure polypeptide possessing lacto-N-biosidase activity.

As described above, the present invention provides the primary structure of lacto-N-biosidase derived from Streptomyces sp 142, and the gene structure thereof. The elucidation of the gene structure of the present invention permits the biotechnological production of a polypeptide possessing lacto-N-biosidase activity. By the use of the present method using recombinant DNA technology, a highly pure polypeptide possessing lacto-N-biosidase activity can be produced at low cost.

EXAMPLES

The following examples illustrate the present invention but are not intended to limit the invention in any manner.

Example 1

Cloning of Lacto-N-biosidase Structure Gene (1) Extraction and Purification of Genomic DNA A strain of Streptomyces sp142 (FERM BP-4569), a lacto-N-biosidase producer, was inoculated to 20 ml of a medium consisting of 1% L-fucose, 0.01% yeast extract, 0.03% peptone, 0.05% $MgSO_4$ $7H_2O$ and 0.1% $KH_2PO_4$, pH 7.8, and cultured at 30° C. for 44 hours. After cultivation, the culture broth was centrifuged to collect cells, which were then immersed in liquid nitrogen and completely milled in a mortar. The milled cells were added little by little to a 10-fold volume (relative to the wet cell volume) of extracting buffer [10 mM Tris-HCl (pH 8.0), 100 mM EDTA, 20 µg/ml RNase A, 0.5% SDS] with gentle stirring; 100 µl of 10 mg/ml proteinase K was then added, followed by incubation at 37° C. for 1 hour. After the mixture was allowed to cool to room temperature, an equal volume of a 1:1 mixture of phenol and chloroform, saturated with TE buffer [10 mM Tris-HCl, 1 mM EDTA, pH 8.0], was added, followed by gentle stirring. After the mixture was centrifuged at 3,000 rpm for 10 minutes, the supernatant was recovered (hereinafter referred to as phenol extraction). This procedure was repeated in 2 cycles; to the water layer was added a 0.6-fold volume of isopropyl alcohol, followed by centrifugation at 14,000 rpm for 1 minute, after which the mixture was rinsed with 70% ethanol and gently dried in air. About 440 µg of genomic DNA was thus obtained.

(2) Determination of Partial Amino Acid Sequence of Lacto-N-biosidase

Lacto-N-biosidase of Streptomyces sp142 as purified by the method described in the Journal of Biological Chemistry, 268, 18560–18566 (1993) was directly subjected to amino acid sequencing by gas phase Edman degradation by a Protein Sequencer 476A produced by Applied Biosystems to determine the N-terminal amino acid sequence LN-N2 (SEQ ID NO:3). After being pyridylethylated [1 nmol of lacto-N-biosidase protein was applied to a desalting column (Fast Desalting Column PC3.2/10, Pharmacia), previously equilibrated with 450 mM N-ethylmorpholine/formate buffer, pH 8.5, and eluted with the same buffer; the resulting eluate was collected in a glass vial and concentrated to dryness; separately, 10 µl of pyridine, 2 µl of 4-vinylpyridine, 2 µl of tri-N-butylphosphine and 10 µl of water were added to a glass test tube larger in diameter than the vial; the sample-containing glass vial was placed in this glass test tube; after the glass test tube was sealed, a reaction was carried out at 100° C. for 5 minutes; after completion of the reaction, the glass vial was taken out from the test tube and thoroughly dried; the resulting pyridylethylated product was used for trypsin digestion], the enzyme protein was digested with TPCK trypsin [40 µl of a 10 mM Tris-HCl buffer (pH 7.5) containing 4 M urea, 50 µl of a 10 mM Tris-HCl buffer (pH 7.5), 10 µl of 0.1 M calcium chloride, and 2 pmol of TPCK trypsin were added to the glass vial, followed by overnight reaction at 37° C.]; from the resulting digest, peptide fragments were separated and purified by HPLC (Smart System, produced by Pharmacia; column, mRPC C2/C18, SC2.1/10; flow rate, 1 ml/min; solvent A, 0.1% trifluoroacetic acid solution; solvent B, acetonitrile containing 0.1% trifluoroacetic acid; elution was conducted on a density gradient from 0% of eluent B at the time of sample application to 10% of eluent B at the time of completion of sample application, after which the eluent B concentration was increased to 60% over an 85-minute period). Each peptide fraction was subjected to amino acid sequencing to determine the partial amino acid sequences LN-6 (SEQ ID NO:7), LN-7 (SEQ ID NO:8), LN-29 (SEQ ID NO:9) and LN-46 (SEQ ID NO:10).

(3) Cloning of DNA Fragment Containing Lacto-N-biosidase Gene

Fifty milligrams of genomic DNA as prepared in (1) above was digested with restriction enzymes BamHI, PstI, SacI and SalI, each in an amount of 120 U, at 37° C. for 2 hours, followed by 4 hours of reaction with addition of 60 U of each enzyme. This reaction mixture was subjected to phenol extraction; a portion of the resulting extract, equivalent to 10 mg of DNA, was subjected to 0.7% agarose gel electrophoresis, followed by Southern blotting (see Idenshi Kenkyuho II, pp. 218–221, Tokyo Kagaku Dojin) to transfer the DNA onto a nylon membrane of Amersham Corporation (trade name Hybond-N+). The membrane was prepared in duplicate.

The hybridization probes used were synthetic oligonucleotides LN-P7 (SEQ ID NO:11) and LN-P46-2 (SEQ ID NO:12), respectively synthesized on the basis of the partial amino acid sequences LN-7 (SEQ ID NO:8) and LN-46 (SEQ ID NO:10) determined in (2) above. Using a MEGA-LABEL kit (produced by Takara Shuzo), 5 pmol of each of these synthetic oligonucleotides was labeled with $^{32}P$.

The above-prepared pair of membranes were each subjected to prehybridization in a solution containing 6× SSC (1× SSC is a solution of 8.77 g of NaCl and 4.41 g of sodium citrate in 1,000 ml of water), 0.5% SDS, 100 µg/ml Pacific herring sperm DNA and 5× Denhardt's solution (containing bovine serum albumin, polyvinylpyrrolidone and Ficoll, each at 0.1%) at 65° C. for 3 hours, after which each labeled probe was added at a concentration of 0.5 pmol/ml, followed by overnight hybridization at 65° C. Each membrane was then washed in 6× SSC at room temperature for 10 minutes, in 2× SSC and 0.1% SDS at room temperature for 10 minutes and in 0.2× SSC and 0.1% SDS at 45° C. for 30 minutes; after excess water was removed, the filter was exposed to an imaging plate (produced by Fuji Photofilm) for 45 minutes, followed by detection using a BAS 2000 imaging analyzer (produced by Fuji Photofilm). As a result, a number of bands that hybridized to the respective probes appeared at positions corresponding to about 8 kb for the BamHI digest, about 3 kb for the PstI digest, about 7.5 kb for the SacI digest, and about 1.8 kb for the SalI digest.

The following experiment was conducted using the PstI and SalI digests, because they are easy to handle. Ten milligrams of genomic DNA, previously digested with restriction enzymes, was subjected to 0.7% agarose gel electrophoresis, and a portion corresponding to the band obtained in the above-described hybridization was cut out. This portion was extracted and purified using an EASYTRAP kit (produced by Takara Shuzo); the resulting DNA fragment was inserted to the PstI or SalI site of pUC19.

*Escherichia coli* JM109 was transformed with this plasmid and cultured on 3 agar plates of 8.5 cm in diameter overnight to form 200 to 1,000 colonies per dish, which were then transferred onto a nylon membrane of Amersham Corporation (trade name Hybond-N) placed on a medium plate. After being incubated at 37° C. for 4.5 hours, the nylon membrane was subjected to denaturation treatment for 5 minutes on filter paper, previously immersed in a solution of 0.5 M NaOH and 1.5 M NaCl, then subjected to neutralization treatment for 5 minutes on filter paper, previously immersed in a solution of 0.5 M Tris-HCl buffer (pH 7.0) and 3 M NaCl, followed by rinsing with 2× SSC. Using this nylon membrane and synthetic oligonucleotide LN-P7 (SEQ ID NO:11), hybridization was conducted under the same conditions as those described above; several positive signals were obtained for each dish. Next, *Escherichia coli* cells on and near the positive signals were transferred from the original plate to a new plate and allowed to form colonies, followed by repetition of the same procedure as that described above, whereby 6 colonies providing a positive signal were isolated. Of these 6 colonies, 2 contained the PstI fragment (designated as P44 and P80), and the other 4 contained the SalI fragment (designated as S6, S39, S63 and S100).

Plasmid DNAs were prepared from the above-obtained clones by the alkali lysis method, and designated as pULNBP44, pULNBP80, pULNBS6, pULNBS39, pULNBS63 and pULNBS100, respectively. These plasmid DNAs were digested with several restriction enzymes and subjected to electrophoresis to analyze the cleavage patterns. As a result, pULNBP44 and pULNBP80 were found to have a total of 14 restriction enzyme sites, including those for HincII, KpnI and SalI. Also, pULNBS6, pULNBS39, pULNBS63 and pULNBS100 were found to have such restriction enzyme sites as those for HincII, KpnI and SalI. This analysis demonstrated that the plasmid pULNBP44 is identical with pULNBP80, pULNBS6, pULNBS39, pULNBS63 and pULNBS100 in terms of DNA insert, and that the PstI fragment and the SalI fragment mutually overlap over almost the entire length. In consideration of this fact, subsequent analysis was conducted mainly on pULNBP80, and as to the rest region pULNBP80 did not cover, pULNBS6 was used instead. These clones were digested with appropriate restriction enzymes and subjected to self-ligation using a ligation kit (produced by Takara Shuzo) to yield various deletion variants. Base sequencing of these variants by the dideoxy method revealed a sequence encoding a portion of lacto-N-biosidase involving the inserts of 2 clones. Specifically, base sequences encoding the partial amino acid sequences LN-7 (SEQ ID NO:8), LN-29 (SEQ ID NO:9) and LN-46 (SEQ ID NO:10) were found therein, but no base sequences encoding the N-terminal amino acid sequence LN-N2 (SEQ ID NO:3) or the partial amino acid sequence LN-6 (SEQ ID NO:7) were found.

(4) Cloning of DNA Fragment Containing Full-length Lacto-N-biosidase Gene

To screen for a DNA fragment encoding a portion near the N-terminus lacked in pULNBP80 in order to cover the full-length region of the lacto-N-biosidase gene, southern hybridization was further conducted in the same manner as that described in (3) above.

Since base sequencing had revealed that pULNBS6 contains a DNA sequence near the N-terminus of the lacto-N-biosidase gene longer by about 100 bp than that contained in pULNBP80, the about 100 bp portion was used as a probe.

Specifically, pULNBS6 was digested with PstI and SalI and subjected to 3% agarose gel electrophoresis; the resulting DNA fragment of about 100 bp length was cut out. The DNA fragment was extracted and purified using Suprec 01 (produced by Takara Shuzo) and labeled with $^{32}$P using a MEGALABEL kit (produced by Takara Shuzo). A pair of filters prepared in the same manner as that described in (3) above were each subjected to prehybridization in a solution containing 6× SSC [1× SSC is a solution of 8.77 g of NaCl and 4.41 g of sodium citrate in 1 L of water), 0.5% SDS, 100 μg/ml Pacific herring sperm DNA and 5× Denhardt's solution (containing bovine serum albumin, polyvinylpyrrolidone and Ficoll, each at 0.1%) at 68° C. for 3 hours, after which each labeled probe was added at a concentration of 0.1 pmol/ml, followed by overnight hybridization at 68° C. Each filter was then washed in 6× SSC at room temperature for 10 minutes, in 2× SSC and 0.1% SDS at room temperature for 10 minutes, and in 0.2× SSC and 0.1% SDS at 50° C. for 20 hours; after excess water was removed, the filter was exposed to an imaging plate (produced by Fuji Photofilm) for 45 minutes, followed by detection using a BAS 2000 imaging analyzer (produced by Fuji Photofilm). As a result, a number of bands that hybridized to the respective probes appeared at positions corresponding to about 8 kb for the BamHI digest, about 3 kb for the PstI digest, about 7.5 kb for the SacI digest, and about 1.8 kb for the SalI digest. The following experiment was conducted using the PstI digest, because it is easy to handle.

Ten milligrams of genomic DNA, previously digested with PstI in the same manner as that described in (3) above, was subjected to 0.7% agarose gel electrophoresis, and a portion corresponding to the band obtained in the above-described hybridization was cut out. This portion was extracted and purified using an EASYTRAP kit (produced by Takara Shuzo); the resulting DNA fragment was inserted to the PstI site of pUC19.

*Escherichia coli* JM109 was transformed with this plasmid and cultured on 3 round Petri dishes 8.5 cm in diameter overnight to form 200 to 1,000 colonies per dish, which were then transferred onto a nylon membrane of Amersham Corporation (trade name Hybond-N) placed on a medium plate. After being incubated at 37° C. for 4.5 hours, the nylon membrane was subjected to denaturation treatment for 5 minutes on filter paper, previously immersed in a solution of 0.5 M NaOH and 1.5 M NaCl, then subjected to neutralization treatment for 5 minutes on filter paper, previously immersed in a solution of 0.5 M Tris-HCl buffer (pH 7.0) and 3 M NaCl, followed by rinsing with 2× SSC. Using this nylon membrane and the about 100 bp PstI-SalI DNA fragment of pULNBS6, hybridization was carried out under the same conditions as those described above; several positive signals were obtained for each dish. Next, *Escherichia coli* cells on and near the positive signals were transferred from the original plate to a new plate and allowed to form colonies, followed by repetition of the same procedure as that described above, whereby 6 colonies providing a positive signal were isolated (designated as P2-17, P2-37, P2-47, P2-67, P2-77 and P2-87).

Figure 1A:
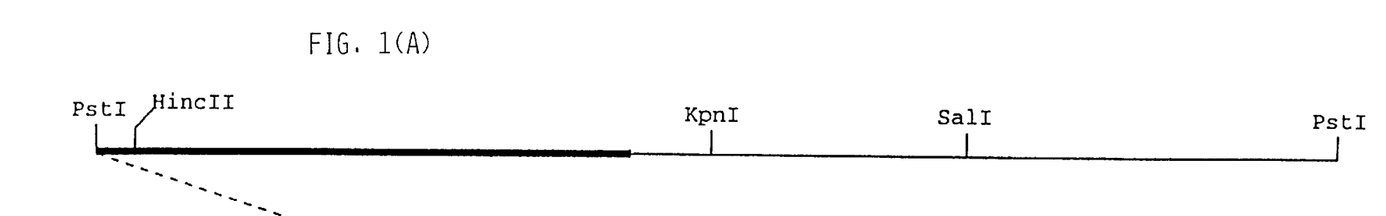
Figure 1B:
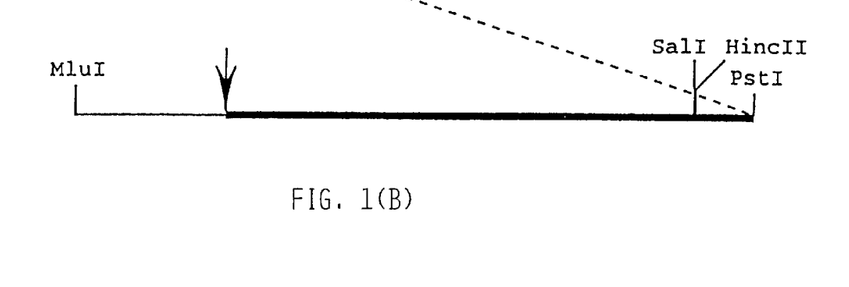

Plasmid DNAs were prepared from the thus-obtained clones by the alkali lysis method, and designated as pULNBP2-17, pULNBP2-37, pULNBP2-47, pULNBP2-67, pULNBP2-77 and pULNBP2-87, respectively. These plasmid DNAs were digested with several restriction enzymes and subjected to electrophoresis to analyze the cleavage patterns. As a result, the PstI inserts of these plasmids were found to have a total of 15 restriction enzyme sites, including those for HincII, SacI, SalI, SmaI and XhoI. It was also found that pULNBP2-17, pULNBP2-37, pULNBP2-67 and pULNBP2-87 showed exactly the same restriction enzyme cleavage patterns as those of pULNBP2-47, pULNBP2-67 and pULNBP2-77, respectively, although the orientation of PstI fragment insertion was reversed. These findings suggested that the former gene fragments are identical with the latter. The following analysis was therefore conducted on pULNBP2-17 only.

pULNBP2-17 was digested from both ends, or digested with appropriate restriction enzymes, then subjected to self-ligation using a ligation kit (produced by Takara Shuzo) to yield various deletion variants. Base sequencing of these variants by the dideoxy method revealed the presence of an about 100 bp base sequence between the PstI and SalI sites of pULNBS6, and the presence of base sequences encoding the N-terminal amino acid sequence LN-N2 (SEQ ID NO:3) and the partial amino acid sequence LN-6 (SEQ ID N0:7). Furthermore, a 1920 bp reading frame was found over the portion between the PstI insert of pULNBP80 and the PstI insert of pULNBP2-17, both determined in (3) above. Within this reading frame, was found all the sequences determined by amino acid sequencing of lacto-N-biosidase in (2) above. The entire base sequence of the lacto-N-biosidase gene was thus determined. The results are given in FIG. 1, which shows the restrict ion enzyme map for the PstI-KpnI region in the PstI insert of pULNBP80, represented by "A", and for the MluI-PstI region in the PstI insert of pULNBP2-17, represented by "B", with the position of the lacto-N-biosidase gene. In FIG. 1, the arrow indicates the translation initiation point for lacto-N-biosidase; the bald line indicates the region that encodes lacto-N-biosidase. By combining "A" and "B", the full-length of the lacto-N-biosidase gene can be known. An example of the base sequences encoding lacto-N-biosidase is shown in SEQ ID NO:2; the amino acid sequence that this base sequence encodes is shown in SEQ ID NO:1.

Example 2

Construction of Lacto-N-biosidase Expression Plasmid (1) Construction of Plasmid Containing Full-length Lacto-N-biosidase Gene To construct a plasmid containing the full-length lacto-N-biosidase gene, the plasmid pULNBP2-17 as obtained in Example 1 was digested with PstI, then subjected to 1% agarose gel electrophoresis; the PstI fragment was cut out and extracted and purified, Next, the plasmid pULNBP80 as obtained in Example 1 was digested with KpnI, and subjected to self-ligation using a ligation kit (produced by Takara Shuzo), followed by transformation into *Escherichia coli* JM109 strain. From the cell culture, the plasmid DNA pULNBP80Kpn was prepared by the alkali lysis method. This DNA was digested with PstI. The PstI fragment obtained from the plasmid pULNBP2-17 was inserted in the resulting PstI digest, followed by transformation into *Escherichia coli* JM109 strain. From the cell culture, the plasmid DNA was isolated by the alkali SDS method; the presence of the insert was confirmed by PstI digestion, and the orientation of the insert was confirmed by SacI digestion. The thus-obtained plasmid containing the full-length lacto-N-biosidase gene was designated as pLNBP-K.

The *Escherichia coli* JM109 strain with pLNBP-K incorporated thereto is referred to as *Escherichia coli* JM109/pLNBP-K, and has been deposited under accession number FERM BP-5333 at the National Institute of Bioscience and Human-Technology, Agency of Industrial Science and Technology, Ministry of International Trade and Industry.

(2) Construction of Expression Plasmid for Lacto-N-biosidase

Next, to construct an expression plasmid for lacto-N-biosidase, the synthetic oligonucleotide primers LNBP-M (SEQ ID NO:13) and LNB-SRV (SEQ ID NO:14) were designed and synthesized. The primer LNBP-M is a 39 mer having a HindIII site and NcoI site upstream the 24 mer corresponding to base sequence at position 106–129 of SEQ ID NO:2 in the 5'-3' direction, while the primer LNB-SRV is a 21 mer synthetic DNA corresponding to base sequence at position 301–321 of SEQ ID NO:2 in the 3'-5' direction.

As a template, about 10 ng of the plasmid pULNBP2-17MluE as obtained in Example 1 (pULNB2-17MluE obtained by digesting the plasmid pULNB2-17 of Example 1 with MluI and EcoRI, blunting both ends, and conducting self-ligation) was mixed with 10 µl of the buffer for 10-fold dilution (supplied in the Gene Amp kit), 16 µl of a 1.25 mM dNTP mixture, 20 pmol of the primer LNBP-M, 20 pmol of the primer LNB-SRV and 2.5 U of Takarataq, followed by the addition of sterile water to obtain 100 µl of a solution. This mixed solution was subjected to an amplifying reaction using an automated gene amplifier (DNA Thermal Cycler 480, produced by Takara Shuzo). A PCR reaction was carried out by repeating a cycle of denaturation at 94° C. for 1 minute, primer annealing at 60° C. for 2 minutes and synthesis at 72° C. for 1.5 minutes in 25 cycles. After 10 µl of the reaction mixture was subjected to 3% agarose gel electrophoresis, DNA was stained with ethidium bromide; an amplified 231 bp DNA fragment was detected as expected. The remaining portion of the PCR reaction mixture was concentrated by ethanol precipitation, after which it was digested with HindIII and SmaI, then inserted to the HindIII-SmaI site of the plasmid pLNBP-K as obtained in Example 2-(1), followed by transformation into *Escherichia coli* JM109 strain. From the cell culture, the plasmid DNA was isolated by the alkali SDS method; the presence of the insert was confirmed by HindIII and SmaI digestion, and the base sequence of the insert was confirmed by the dideoxy method. The thus-obtained lacto-N-biosidase expression plasmid was designated as pLNBM.

The thus-obtained *Escherichia coli* JM109/pLNBM was inoculated to 5 ml of an L medium containing 100 µg/ml ampicillin and subjected to shaking culture at 37° C.; upon reach of a turbidity at O.D. 600=0.5, IPTG (isopropyl-1-thio-β-D-galactopyranoside) was added at a final concentration of 1 mM, followed by overnight shaking culture at 37° C. After the cultivation, 1 ml of the culture broth was centrifuged; collected cells were washed with a 50 mM potassium phosphate buffer of pH 6.0. The cells were then suspended in 0.5 ml of the same buffer and disrupted by ultrasonication. After centrifugation, the supernatant was recovered to yield an *Escherichia coli* extract. Analysis of this extract and precipitates by SDS polyacrylamide gel electrophoresis failed to detect a band corresponding to lacto-N-biosidase; also, the activity in the extract was determined by the method described in the Proceedings of the National Academy of Sciences of the USA, 89, 8512–8516 (1992), but no lacto-N-biosidase activity was detected.

Construction of another expression plasmid was tried. After the plasmid pLNBM was digested with KpnI, its ends were blunted, followed by further digestion with HindIII and subsequent 1% agarose gel electrophoresis; a HindIII-KpnI fragment was cut out and extracted and purified. After pET23d (produced by Novagen), an expression vector incorporating the T7 promoter, was digested with NotI, its ends were blunted, followed by further digestion with HindIII. To the resulting digest, the HindIII-KpnI fragment of the plasmid pLNBM was inserted, followed by transformation into *Escherichia Coli* HB101 strain (produced by Takara Shuzo). From the cell culture, the plasmid DNA was isolated by the alkali SDS method; the presence of the insert was confirmed by HindIII and XhoI digestion, and the base sequence of the insert was confirmed by the dideoxy method. The thus-obtained lacto-N-biosidase expression plasmid was designated as pELNB101.

The thus-obtained plasmid pELNB101 was transformed into *Escherichia coli* BL21 (DE3) strain. The resulting *Escherichia coli* BL21 (DE3)/pELNB101 was inoculated to 5 ml of an L medium containing 100 µg/ml ampicillin and subjected to shaking culture at 37° C.; upon reach of a turbidity at O.D. 600=0.5, IPTG was added at a final concentration of 1 mM, followed by overnight shaking culture at 37° C. After the cultivation, 1 ml of the culture broth was centrifuged; cells were collected and washed with 50 mM phosphate buffer of pH 6.0. The cells were then suspended in 0.5 ml of the same buffer and disrupted by ultrasonication. After centrifugation, the supernatant was recovered to yield an *Escherichia Coli* extract. Analysis of this extract and precipitates by SDS polyacrylamide gel electrophoresis detected a band assignable to lacto-N-biosidase of 60,000 in molecular weight; also, lacto-N-biosidase activity was detected in the extract. These findings demonstrate that *Escherichia coli* BL21 (DE3)/pELNB101 is capable of expressing the lacto-N-biosidase protein.

There is the possibility that lacto-N-biosidase produced by *Escherichia Coli* BL21 (DE3)/pELNB101 is mostly in the form of an insoluble inclusion body.

(3) Lacto-N-biosidase Expression in *Escherichia Coli* and Purification of Inclusion Body

*Escherichia Coli* BL21 (DE3)/pELNB101 was inoculated to 2 test tubes each containing 5 ml of an L medium containing 100 μg/ml ampicillin and subjected to shaking culture at 37° C. for 5 hours; 5 ml of the cell culture was inoculated to two 2,000 ml conical flasks each containing 500 ml of 2× YT medium, and subjected to overnight rotary shaking culture at 37° C. and 100 rpm. After the cultivation, cells were collected by centrifugation, suspended in 25 ml of a 10 mM Tris-HCl buffer (STE) containing 0.1 M NaCl and 1 mM EDTA, and disrupted by ultrasonication. After the suspension of disrupted cells was centrifuged, the insoluble fraction containing inclusion bodies was collected, washed with 30 ml of STE, and centrifuged; the resulting precipitates were suspended in 30 ml of a 1 M sucrose solution. The resulting suspension was centrifuged at 18,000×g for 30 minutes to yield precipitates containing the inclusion bodies. The precipitates were suspended in 40 ml of a 2% Triton X-100 solution containing 10 mM EDTA and kept standing at 4° C. overnight. After the insoluble substances were collected by centrifugation, the same procedure as that described above was repeated to wash the inclusion bodies. SDS polyacrylamide gel electrophoresis of a portion of the inclusion bodies thus obtained demonstrated more than half amount of the protein migrated to a position corresponding to a molecular weight of about 60,000, suggesting that more than half amount of the protein of the inclusion body fraction obtained was recombinant lacto-N-biosidase. The amount of this recombinant lacto-N-biosidase protein is assumed to be about 10 mg per 100 ml of culture broth, as estimated in comparison with the density of the band of the bovine serum albumin analyzed simultaneously.

(4) Solubilization of Inclusion Bodies and Refolding of their Proteins

About 10 mg (equivalent to 100 ml of culture broth) of the inclusion bodies obtained were suspended in 3 ml of a 20 mM potassium acetate buffer (pH 5.5) containing 8 M urea, 10 mM dithiothreitol and 0.5 M KCl, and solubilized by stirring at room temperature for 1 hour. After the residual insoluble substances were removed by centrifugation, 50 μl of the supernatant was diluted with 5 ml of a 20 mM potassium acetate buffer (pH 5.5) and kept standing at 15° C. overnight.

(5) Assay of Lacto-N-biosidase Activity

With the resulting solution, lacto-N-biosidase activity was determined according to the method described in a literature [Proceeding of the National Academy of Sciences of the USA, 89, 8512–8516(1992)].

Specifically, a sample solution of the enzyme was incubated for 20 minutes with 2 μm PA-lacto-N-tetraose (Galβ1-3GlcNAcβ1-3Galβ1-4Glc-PA; manufactured by Takara Shuzo; hereinafter referred to as PA-oligosaccharide) at 37° C. in 10 μl of 0.1 M potassium phosphate buffer (pH 6.0). Then, 40 μl of 1% trifluoroacetic acid was added to the reaction mixture to terminate the reaction.

A portion containing 10 pmol of PA-oligosaccharide was then analyzed by HPLC with an amino-silica column or a $C_{18}$-silica column, and the labeled product was detected by fluorescence.

The degree of hydrolysis was calculated from the peak areas of the substrate and this product in comparison with the peak area of the corresponding standard PA-oligosaccharide.

One unit of activity was defined as the amount of enzyme needed to release 1 pmol of product per min under the conditions described above.

As the results of the assay, lacto-N-biosidase activity of the solution was found to be 0.06 mU/ml. This means that about 180 mU of recombinant lacto-N-biosidase was obtained from 1 L of the culture of *Escherichia coli* BL21 (DE3)/pEL NB101 harboring the gene of the invention.

Other modifications of the above described embodiments of the invention which are obvious to those skilled in the art are intended to be within the scope of the following claims.

What is claimed is:

1. An isolated DNA encoding a polypeptide possessing lacto-N-biosidase activity, the isolated DNA being selected from the group consisting of:
 (a) a DNA having a nucleotide sequence encoding the amino acid sequence of SEQ ID NO:1;
 (b) a DNA having the nucleotide sequence of SEQ ID NO:2; and
 (c) a DNA which hybridizes to (b) above at 65° C. for 20 hours in a solution containing 6× SSC, 1% sodium lauryl sulfate, 100 µg/ml salmon sperm DNA and 5× Denhardt's solution.

2. The isolated DNA according to claim 1, wherein the polypeptide is derived from a strain of the genus Streptomyces.

3. The isolated DNA according to claim 2, wherein the strain is Streptomyces sp 142 (FERM BP-4569).

4. The isolated DNA according to claim 1, wherein said DNA encodes a polypeptide of SEQ ID NO:1.

5. The isolated DNA according to claim 4, having a DNA sequence of SEQ ID NO:2.

6. An expression vector which comprises the DNA as defined in claim 1, wherein the expression vector propagates in a procaryotic or eucaryotic cell.

7. The expression vector according to claim 6, wherein the polypeptide encoded by the DNA has the amino acid sequence of SEQ ID NO:1.

8. The expression vector according to claim 6, containing a DNA sequence of SEQ ID NO:2.

9. A cell of a procaryote or eucaryote transformed with an expression vector as defined in claim 6.

10. The cell according to claim 9, wherein a polypeptide encoded by the expression vector has the amino acid sequence of SEQ ID NO:1.

11. The cell according to claim 9, wherein the expression vector contains a sequence of SEQ ID NO:2.

12. The cell according to claim 9, wherein said eucaryote or said procaryote is selected from the group consisting of microorganisms, animal cells and plant cells.

13. The cell according to claim 9, wherein said eucaryote is *Escherichia coli*.

14. A method for producing a polypeptide possessing lacto-N-biosidase activity comprising the steps of:
 (a) culturing the cell of claim 9; and
 (b) recovering the polypeptide possessing lacto-N-biosidase activity from the culture obtained in Step (a).

15. A synthetic oligonucleotide probe or primer which specifically hybridizes with the isolated DNA of claim 1 at 65° C. for 20 hours in a solution containing 6× SSC, 1% sodium lauryl sulfate, 100 µg/ml salmon sperm DNA and 5× Denhardt's solution.

\* \* \* \* \*